United States Patent [19]

Suskovic et al.

[11] Patent Number: 5,153,173
[45] Date of Patent: Oct. 6, 1992

[54] N-ACYL DERIVATIVES OF THE PEPTIDOGLYCAN MONOMER, PHARMACEUTICALLY ACCEPTABLE SALTS THEREOF, THEIR PREPARATION AND USE AS IMMUNOMODULATORS AND IMMUNOADJUVANTS

[75] Inventors: Božidar Šušković; Radmila Naumski; Vera Gomerčić; Zdenko Mubrin, all of Zagreb, Yugoslavia

[73] Assignee: Pliva Farmaceutska, Zagreb, Yugoslavia

[21] Appl. No.: 499,586

[22] Filed: Mar. 27, 1990

[30] Foreign Application Priority Data

Mar. 27, 1990 [YU] Yugoslavia .............. P-626/89

[51] Int. Cl.$^5$ .............. A61K 37/02; C07K 9/00; C07K 3/08; C07K 7/02
[52] U.S. Cl. .............. 514/8; 530/322; 530/329; 530/332; 530/333
[58] Field of Search .............. 514/8; 530/322, 329, 530/332, 333

[56] References Cited

U.S. PATENT DOCUMENTS 4,545,932 10/1985 Takase et al. .............. 530/322

OTHER PUBLICATIONS

R. Furuta et al., *Agric. Biol. Chem.* 50: 2561-2572, 1986.
A. Adam et al., *Medicinal Research Reviews* 4: 111-152, 1984.
E. Grochowski et al., *Synthesis* 4: 277-279, 1977.
E. Vinogradova et al., *Chemical Abstracts* 70: 393, Abstract #115536s, 1969.
E. Vinogradova et al., *Chemical Abstracts* 70: 394-395, #115537t, 1969.
Z. Haque et al., *Agric. Biol. Chem.* 46: 597-599, 1982.
H. Okumura et al., *Agric. Biol. Chem.* 47: 847-854, 1983.
M. Bodanszky, *The Peptides*, vol. 1: 105-196, 1979.
I. Hrsak et al., *Eur. J. Cancer Clin. Oncol.* 19: 681-686, 1985.
G. Sava et al., *Cancer Immunol. Immunother.* 15: 84-86, 1983.
G. Sava et al., *Cancer Immunol. Immunother.* 18: 49-53, 1984.
I. Hrsak et al., *Z. Immun.-Frosch.* 155: 312-318, 1979.
I. Hrsak et al., *Periodicum Biologorum* 82: 147-151, 1980.
E. Lederer, *J. Med. Chem.* 23: 819-825, 1980.
K. Nishimura, *Infection and Immunity* 47: 665-669, 1985.
M. Parant, *Int. J. Immunotherapy* 1: 11-16, 1985.
I. Tizard, *Immunology: An Introduction*, pp. 159-161, 1984.

A. Adam, ISI Atlas of Science: Immunology, vol. 1, pp. 205-214, 1988.
M. Parant et al., *Eur. J. Clin. Study Treat. Inf.* 12: 230-234, 1984.
C. Leclerq et al., *Immunochemistry of Viruses*, pp. 13-28, 1985.
P. Lefrancier et al., "Chemistry of Synthetic Immunomodulant Muramyl Peptides", pp. 2-47, in *Fortschritte d. Chem. org. Naturst.* 40, 1981.

*Primary Examiner*—Robert A. Wax
*Assistant Examiner*—Stephen Walsh
*Attorney, Agent, or Firm*—Pollock, Vande Sande & Priddy

[57] ABSTRACT

N-acyl derivatives of the peptidoglycan monomer of the formula I

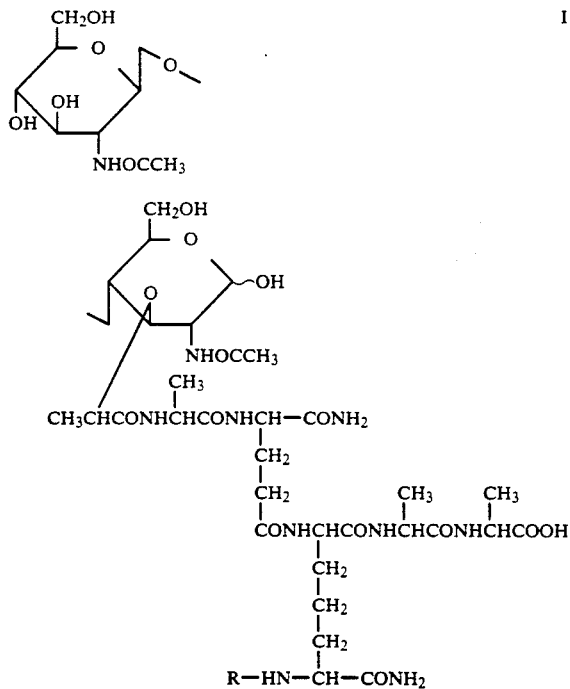

wherein R stands for an acyl group of a straight-chain $C_{2-18}$ alkyl carboxylic acid, or a branched-chain $C_{5-18}$ alkyl carboxylic acid, or an unsaturated $C_{12-18}$ alkenyl carboxylic acid, or a $C_{7-12}$ aromatic carboxylic acid, and pharmaceutically acceptable salts thereof. A process for the preparation thereof and their use in pharmaceuticals, which are particularly indicated as immunomodulators and immunoadjuvants in humans and animals.

14 Claims, No Drawings

N-ACYL DERIVATIVES OF THE PEPTIDOGLYCAN MONOMER, PHARMACEUTICALLY ACCEPTABLE SALTS THEREOF, THEIR PREPARATION AND USE AS IMMUNOMODULATORS AND IMMUNOADJUVANTS

This invention relates to new N-acyl derivatives of the peptidoglycan monomer (PGM) and pharmaceutically acceptable salts thereof, to a process for the preparation thereof and to the use of the new compounds of the invention in pharmaceuticals that are particularly indicated as immunomodulators and immunoadjuvants.

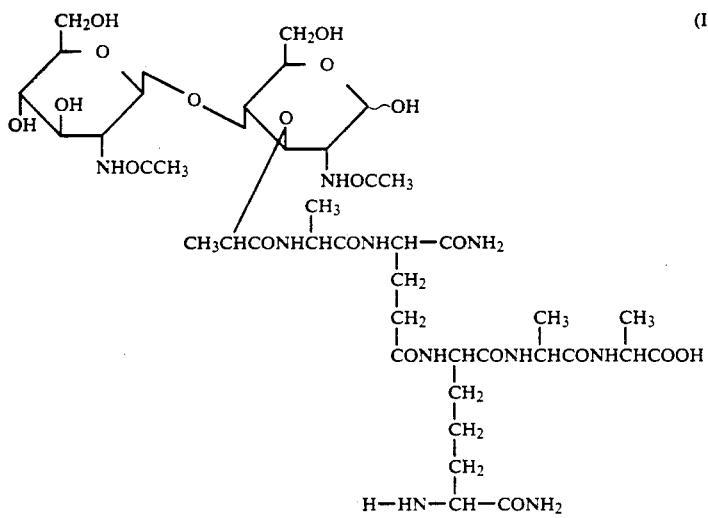

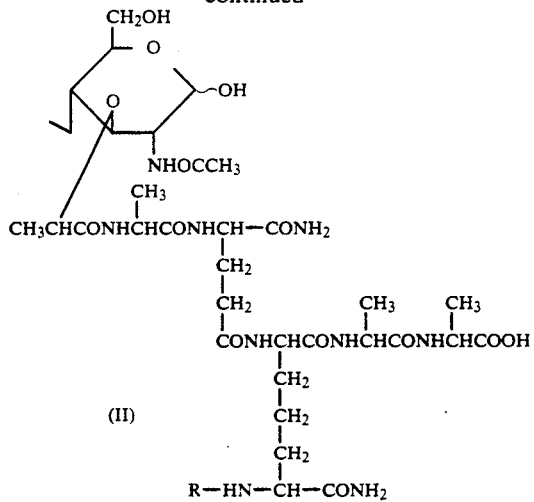

(Carbohydr. Res. 110 (1982), 320–325) exhibits an immunomodulating (Z. Immun.-Forsch. 155 (1979), 312-328) as well as antimetastatic activity (Eur. J. Cancer On col. 19 (1983), 681-686; Cancer Immunol. Immunother. 15 (1983), 84-86; Cancer Immunol. Immunother. 18 (1984), 49-53); it is nontoxic and apyrogenous. It is well water-soluble but insoluble in organic solvents. Owing to its highly hydrophilic and lipophobic character it is not able to penetrate through the lipophilic membranes in the organism. The extent of hydrophilicity and lipophilicity in such compounds might significantly influence their activity.

One object of the present invention are new N-acyl derivatives of the peptidoglycan monomer of the formula I

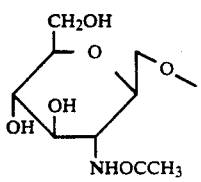

(I)

wherein R stands for an acyl group of a straight-chain $C_{2-18}$ alkyl carboxylic acid, or a branched-chain $C_{5-18}$ alkyl carboxylic acid, or an unsaturated $C_{12-18}$ alkenyl carboxylic acid, or a $C_{7-12}$ aromatic carboxylic acid, and pharmaceutically acceptable salts thereof.

R in the meaning of an acyl in a straight-chain $C_{2-18}$ alkyl carboxylic acid in formula I stands e.g. for an acetyl, capriloyl, caprinoyl, lauroyl, palmitoyl, stearoyl.

R in the meaning of an acyl in a branched-chain $C_{5-18}$ alkyl carboxylic acid in formula I stands preferably for pivaloyl.

R in the meaning of an acyl in an unsaturated $C_{12-18}$ alkenyl carboxylic acid in formula I stands preferably for oleoyl.

R in the meaning of an acyl in a $C_{7-12}$ aromatic carboxylic acid in formula I stands preferably for benzoyl.

The pharmaceutically acceptable salts of the new N-acyl derivatives of the peptidoglycan monomer (PGM) also comprise their salts with inorganic or organic bases, such as alkali metal salts (e.g. sodium salts, potassium salts), alkaline-earth metal salts (e.g. calcium salts), ammonium salts and organic base salts (e.g. ethanolamine salts, triethanolamine salts) and other physiologically tolerated salts.

In the process for the preparation of the new N-acyl derivatives of PGM of the formula I there have been applied per se known methods of acylating PGM of the formula II by means of reacting with the corresponding acid

   (III)

wherein R has the meaning as defined in formula I, and wherein the acid is in activated form, e.g. in the form of an anhydride, especially in the form of an active ester, such as those formed in the interaction of the acid and N-hydroxysuccinimide, N-hydroxybenzotriazole, N-hydroxyphthalimide and similar alcohols. The preparation of active esters is performed in the presence of a dehydration agent such as dicyclohexylcarbodiimide (DCC) and other coventional carbodiimides as described in the literature, N,N-carbonyldiimidazole, p-toluenesulfonate and other known sulfonates. The reaction conditions for the use of such agents are described in the literature. The reactions with carbodiimides are preferred as they are performed at 20°-25° C. and give high yields. The acylation of PGM with e.g. acetic acid anhydride is performed in the presence of a base such as sodium hydrogen carbonate, whereas the acetylation with the corresponding active acid ester is performed in an inert solvent such as dimethylformamide (DMF) in the presence of an organic base as catalyst. The PGM and the active ester are used within a ratio of 1:1.3 to 1:2 (mole/mole) and PGM and the solvent within the ratio of 1:30 to 1:100 (w./v.). The organic base is in the form of an amine, such as e.g. triethylamine (TEA) and it is added to PGM in a ratio of 1:2 to 1:5 (mole/mole). The reaction is performed at a temperature of 20°-25° C. within 24 hours. The reaction is surveyed by thin-layer chromatography (TLC) on a matrix of silica gel as the adsorbent and in a solvent system that is appropriate for the separation of products from the starting reactants, such as the solvent system n-propanol-water 7:3 (v./v.) (system A).

The product is obtained upon the addition of an organic solvent, in which it is not soluble, such as ethyl acetate (EtOAc). It is purified by means of conventional methods, such as column chromatography on various adsorbents, e.g. on silica gel, elution with the afore-said system A or on Sephadex and elution with water.

It is a further object of the present invention to provide pharmaceuticals comprising an active, yet physiologically tolerated dose of the new N-acyl derivative of the peptideglycan monomer (I) or its pharmaceutically acceptable salts and the use thereof in the manufacture of immunomodulation or immunoadjuvant drug formulations. The active compounds may be formulated in combination with a pharmaceutically acceptable carrier. The pharmaceutical compositions are preferably administered parenterally.

The biological activity of the claimed compounds was tested on CBA male mice, 2-2.5 months old. The animals had been adapting to the laboratory conditions at least one week prior to each testing. The effectiveness of the N-acyl derivative of PGM was compared with the results achieved in control mice goups which were administered a physiological solution (negative control) and the original PGM (positive control). All tested substances were administered to the organism by intravenous (i.v.) route in a single dose of 200 μg/mouse and 10 mg/kg resp. The following effects of the immunopharmacological activity were surveyed: spleen weight, number of lymphocytes and number of PFC (plaque forming cells) according to the method of Jerne (in: Cell Bound Antibodies, Whister Institute Press, Philadelphia (1963), p.109). The spleen weight is expressed in mg. The number of the spleen lymphocytes is expressed as the absolute number in 1 ml, whereas the PFC are expressed by way of their total number and by their activity $10^6$ spleen lymphocytes. The test groups and the corresponding control groups resp. comprised each 5-7 mice. The activity of each N-acyl derivative of PGM was examined at least three times in various periods. The statistical analysis was performed with the parametric Student t-test, applying the original computer programme Stat Works. The significance of the differences was assessed by two-tailed test at the level of acceptance equal or less than 5%. The summarized results of the effects of individual N-acyl derivatives on the parameters of immune response are listed in Table 1.

TABLE 1

N ACETYL PGM SUMMARY DATA OF HUMORAL IMMUNITY

| | Group | N | Spleen weight | t/p | No spleen cells | t/p | Abs. PFC | t/p | PFC/l mil Ly | t/p |
|---|---|---|---|---|---|---|---|---|---|---|
| Exp. No. 1 | Control | 17 | 109.1 ± 17.34 | | 37.7 ± 7.56 | | 74.3 ± 34.40 | | 185.0 ± 93.04 | |
| | % | | 100 | | 100 | | 100 | | 100 | |
| | PGM | 17 | 111.7 ± 10.66 | | 35.1 ± 5.06 | | 82.9 ± 31.71 | | 219.1 ± 96.98 | |
| | % | | 102 | | 93 | | 112 | | 118 | |
| | Stearoyl PGM | 18 | 123.6 ± 18.63 | 2.37 | 37.8 ± 6.90 | | 93.4 ± 37.55 | | 219.2 ± 67.11 | |
| | % | | 113 | 0.05 | 100 | | 126 | | 118 | |
| Exp. No. 2 | Control | 11 | 103.3 ± 18.55 | | 38.7 ± 9.16 | | 56.3 ± 26.55 | | 138.3 ± 74.30 | |
| | % | | 100 | | 100 | | 100 | | 100 | |
| | PGM | 11 | 107.5 ± 9.40 | | 35.0 ± 6.01 | | 76.2 ± 32.95 | | 206.9 ± 113.24 | 2.97 |
| | % | | 104 | | 90 | | 135 | | 150 | 0.01 |
| | Control | 18 | 99.8 ± 17.14 | | 34.2 ± 9.45 | | 69.3 ± 42.49 | | 198.3 ± 144.16 | |
| | % | | 100 | | 100 | | 100 | | 100 | |
| | Benzoyl PGM | 19 | 113.4 ± 22.28 | | 34.1 ± 9.56 | | 95.7 ± 28.45 | 2.23 | 282.1 ± 142.64 | 1.78 |
| | % | | 114 | | 100 | | 138 | 0.05 | 142 | 0.1 |
| Exp. No. 3 | Control | 16 | 120.2 ± 17.83 | | 38.8 ± 8.19 | | 55.7 ± 40.52 | | 122.1 ± 80.16 | |
| | % | | 100 | | 100 | | 100 | | 100 | |
| | PGM | 17 | 138.7 ± 11.72 | 3.54 | 472. ± 9.53 | 2.71 | 88.8 ± 72.51 | | 156.1 ± 102.78 | |
| | % | | 115 | 0.01 | 122 | 0.02 | 159 | | 128 | |
| | Capriloyl PGM | 18 | 120.4 ± 12.36 | | 46.1 ± 11.70 | 2.08 | 88.5 ± 75.95 | | 154.2 ± 111.12 | |
| | % | | 100 | | 119 | 0.05 | 159 | | 126 | |
| Exp. No. 4 | Control | 16 | 120.2 ± 17.83 | | 38.8 ± 8.19 | | 55.7 ± 40.52 | | 122.1 ± 80.16 | |
| | % | | 100 | | 100 | | 100 | | 100 | |
| | PGM | 17 | 138.6 ± 11.72 | 3.52 | 47.2 ± 9.52 | 2.71 | 88.8 ± 72.20 | | 156.1 ± 102.78 | |
| | % | | 115 | 0.01 | 122 | 0.02 | 159 | | 128 | |
| | Caprinoyl PGM | 17 | 124.4 ± 16.54 | | 42.1 ± 10.55 | | 81.6 ± 79.80 | | 169.9 ± 151.32 | |
| | % | | 103 | | 109 | | 147 | | 139 | |

TABLE 1-continued

N ACETYL PGM SUMMARY DATA OF HUMORAL IMMUNITY

| | Group | N | Spleen weight | t/p | No spleen cells | t/p | Abs. PFC | t/p | PFC/1 mil Ly | t/p |
|---|---|---|---|---|---|---|---|---|---|---|
| Exp. No. 5 | Control | 15 | 121.3 ± 16.3 | | 57.1 ± 21.44 | | 77.5 ± 28.59 | | 163.6 ± 61.00 | |
| | % | | 100 | | 100 | | 100 | | 100 | |
| | PGM | 18 | 129.5 ± 11.80 | | 49.5 ± 8.98 | | 107.7 ± 57.78 | | 190.4 ± 79.53 | |
| | % | | 107 | | 87 | | 139 | | 116 | |
| | Lauroyl PGM | 18 | 135.5 ± 22.60 | | 45.2 ± 8.50 | 2.16 | 125.4 ± 68.45 | 2.49 | 254.2 ± 132.36 | 2.44 |
| | % | | 112 | | 79 | 0.05 | 162 | 0.02 | 155 | 0.05 |
| Exp. No. 6 | Control | 21 | 128.9 ± 14.26 | | 38.8 ± 8.45 | | 47.1 ± 28.06 | | 105.9 ± 54.24 | |
| | % | | 100 | | 100 | | 100 | | 100 | |
| | PGM | 23 | 134.3 ± 13.9 | | 43.8 ± 7.82 | 2.04 | 56.0 ± 23.14 | | 117.1 ± 48.37 | |
| | % | | 104 | | 113 | 0.05 | 119 | | 111 | |
| | Control | 28 | 119.0 ± 20.93 | | 35.9 ± 9.13 | | 57.8 ± 40.45 | | 152.5 ± 127.38 | |
| | % | | 100 | | 100 | | 100 | | 100 | |
| | Palmitoyl PGM | 28 | 123.4 ± 23.15 | | 39.1 ± 10.92 | | 95.8 ± 75.30 | 2.35 | 266.5 ± 279.40 | 1.95 |
| | % | | 104 | | 109 | | 166 | 0.05 | 175 | 0.1 |
| Exp. No. 7 | Control | 18 | 108.4 ± 16.71 | | 41.2 ± 10.28 | | 86.1 ± 25.80 | | 194.0 ± 79.48 | |
| | % | | 100 | | 100 | | 100 | | 100 | |
| | PGM | 18 | 111.8 ± 10.68 | | 38.8 ± 9.06 | | 87.6 ± 29.76 | | 214.4 ± 95.61 | |
| | % | | 103 | | 94 | | 102 | | 111 | |
| | Oleoyl PGM | 17 | 131.7 ± 14.40 | 4.41 | 42.3 ± 7.96 | | 97.1 ± 41.86 | | 210.8 ± 88.40 | |
| | % | | 121 | 0.01 | 103 | | 113 | | 109 | |
| Exp. No. 8 | Control | 17 | 106.4 ± 12.49 | | 43.8 ± 10.39 | | 77.1 ± 33.81 | | 170.9 ± 93.98 | |
| | % | | 100 | | 100 | | 100 | | 100 | |
| | PGM | 17 | 112.7 ± 10.38 | | 40.9 ± 7.86 | | 76.9 ± 28.55 | | 163.6 ± 72.39 | |
| | % | | 106 | | 93 | | 100 | | 96 | |
| | Acetyl PGM | 18 | 112.3 ± 12.08 | | 41.9 ± 5.66 | | 85.8 ± 33.17 | | 202.7 ± 91.97 | |
| | % | | 106 | | 96 | | 111 | | 119 | |
| Exp. No. 9 | Control | 16 | 117.4 ± 18.71 | | 45.9 ± 10.47 | | 69.2 ± 23.72 | | 139.1 ± 50.43 | |
| | % | | 100 | | 100 | | 100 | | 100 | |
| | PGM | 18 | 121.6 ± 14.54 | | 46.7 ± 7.99 | | 72.8 ± 22.20 | | 141.4 ± 40.57 | |
| | % | | 104 | | 102 | | 105 | | 102 | |
| | Pivaloyl PGM | 18 | 125.5 ± 19.44 | | 42.9 ± 9.82 | | 76.4 ± 24.94 | | 163.8 ± 52.95 | |
| | % | | 107 | | 94 | | 110 | | 118 | |

A statistically significant increase in the spleen weight was found upon the application of the sodium salt of N-stearoyl-PGM and the sodium salt of N-oleoyl-PGM (13% and 21% resp. in comparison to the control values). A relative increase in the spleen weight was also found upon the use of the Na-salt of N-benzoyl-PGM, the Na-salt of N-lauroyl-PGM and the Na-salt of N-pivaloyl-PGM, yet the differences with respect to the control values were not significantly increased though there was a clearly expressed tendency of improved activity of said derivatives. The changes in the number of spleen lymphocytes (absolute number in 1 mL) were different for each derivative. In the mice group which had been administered the Na-salt of N-lauroyl-PGM there was detected a statistically significant reduction of 20% in comparison to the control values. In mice treated with the Na-salt of N-capriloyl-PGM there resulted a statistically significant increase of the number of the spleen lymphocytes (19%). A reduction of 4-6% of the number of spleen lymphocytes was detected in mice upon the administration of the pivaloyl and acetyl derivatives, whereas an increase of 3-9% was found in mice treated with oleoyl, caprinoyl and palmitoyl derivatives of PGM. Although there was evident a certain tendency in the achieved changes, the latter were of no statistical significance. Of no effect upon the number of spleen lymphocytes were the Na-salts of the stearoyl and benzoyl derivatives of PGM. Practically all examined substances effected an increase of PFC, which varied within 10% to 66% over the control values. A statistically significant difference, however, was found only for the Na-salts of the N-benzoyl, N-lauroyl and N-palmitoyl derivatives of PGM. All used substances enhanced the PFC activity, as evident with respect to the number of the spleen lymphocytes and which varied within 9% to 75% over the values found in the control mice group. A statistically significant difference was found for the lauroyl derivative of PGM. A clearly expressed enhancing tendency was found for the benzoyl and acetyl derivatives of PGM, where the differences in comparison to the control values practically reached the statistically significant level ($0.5 < p < 0.1$).

On the basis of the obtained results it may be concluded that all examined N-acyl derivatives of the peptidoglycan monomer exhibit a certain immunostimulating activity, yet the individual derivatives differ in their effectivity. One of the possible interpretations of the variety of the resulting differences in the lymphocyte number and the increase of the spleen weight might reside in the different mechanisms of activity of the PGM and the claimed N-acyl derivatives thereof on the cellular immune system.

The other possible reason might be the fact that they resemble in the mechanism of activity, yet differ in their intrinsic activity. The effect on the humoral immunity is evident from the changes in the PFC activity and differs to a certain extent from the effect on the number of the spleen lymphocytes. A significant effect on the overall PFC activity was found for the benzoyl, lauroyl and palmitoyl derivatives of PGM, which do not essentially change or decrease the number of lymphocytes in 1 mg of the spleen tissue.

The structural modifications of the PGM molecule resulted in a new and non-obvious biological activity of the claimed N-acyl derivatives of PGM, demonstrated in two different ways: a significant effect on the cellular immune response, characteristic of the lauroyl and capriloyl derivatives of PGM; on the other hand the benzoyl, lauroyl and palmitoyl derivatives of PGM were more significantly involved in the humoral immunity. The obtained results demonstrated the superior activity of the lauroyl derivative of PGM due to its effect on the cellular and humoral immunity; in addition it showed a superior activity in comparison with the original PGM, when administered in the same concentration.

The invention is illustrated by the following Examples.

Example 1

Preparation of the NA-salt of N-acetyl-PGM

Into a solution of PGM (500 mg, 0.495 mmole) in water (7 mL) there was added a saturated aqueous solution of sodium hydrogen carbonate (NaHCO, 2.75 ML) and it. The mixture was then concentrated by evaporation at reduced pressure to yield an oily precipitate (0.95 g), which was dissolved in water (2.5 mL) and separated on a column packed with 150 mL of Sephadex G-25 fine, whereupon it was eluted with water. The products comprising fractions were combined and lyophilized. Yield 490 mg (92%).

M.p. 186°–188° C., UV $_{max}$(H$_2$O) (nm); 202; IR$^{KDr}$(cm$^1$): 3400–3240, 1660, 1550, 1410.

$^1$H NMR (D$_2$O) (ppm): 1.90 (s, 3H CH$_3$CONH-A$_2$pm), 186 (s, 3H CH$_3$CONH-Glc), 2.03 (s, 3H CH$_3$CONH-Mur).

Abbreviations:

A$_2$pm = diaminopimelyl
Mur = muramoyl
Glc = glucosaminyl

EXAMPLE 2

Preparation of the N-stearoyl-PGM

Into a solution of PGM (1,546 mg, 1.53 mmole) in DMF (26.6 mL) there were added succinimido-stearate (800 mg, 2.09 mmole) and triethylamine (TEA) (0.4 mL, 2.18 mmole) and it was stirred for 20 hours at 20°–25° C. There resulted a gelatinous suspension, into which there was added dropwise under stirring EtOAc (180 mL) and the stirring was continued for further 5 hours. The precipitate was separated by filtration and dried. Yield 2 g. The product was purified by means of column chromatography on silica gel (25 g) and elution with the solvent system A. The product-comprising fractions were combined and concentrated by the evaporation of the solvent at reduced pressure. Yield 1.44 g (57%).

M.p. 217°–220° C., UV$_{max}$(H$_2$O) (nm): 204; IR$^{KBr}$(cm$^{-1}$): 3280, 2910, 2350, 1635, 1530.

EXAMPLE 3

Preparation of the N-pivaloyl-PGM

Into a solution of PGM (500 mg, 0.495 mmole) in DMF (10 mL) there were added succinimido-pivalate (137 mg, 0.688 mmole) and triethylamine (TEA) (0.13 mL, 0.7 mmole) and it was stirred for 24 hours at 25° C. Into the clear solution there was added dropwise EtOAc (50 mL) and the resulting precipitate was kept stirring for 2 hours and filtered off. The precipitate was washed with EtOAc (2×5 mL) and dried. Yield 550 mg. The product was purified by means of column chromatography on silica gel and elution with the solvent system A. The product-comprising fractions were combined and concentrated by the evaporation of the solvent at reduced pressure. Yield 270 mg (49.8%).

M.p. 202°–204° C., UV$_{max}$(H$_2$O) (nm): 201; IR$^{KBr}$(cm$^{-1}$): 3400, 3300, 3080, 3050, 2980, 1650, 1540.

EXAMPLE 4

Preparation of the N-oleoyl-PGM

Into a solution of PGM (500 mg, 0.495 mmole) in DMF (9 mL) there were added succinimido-oleate (258 mg, 0.679 mmole) and triethylamine (TEA) (0.13 mL, 0.7 mmole) and it was stirred for 24 hours at 25° C. There was added dropwise EtOAc (50 mL) and the resulting precipitate was kept stirring for 3 hours. The precipitate was separated by filtration and dried. Yield 680 mg. The precipitate was purified by means of column chromatography on silica gel and elution with the solvent system A. The product-comprising fractions were combined and concentrated by the evaporation of the solvent at reduced pressure.

Yield 0.345 g (54,6%).
M.p. 204°–206° C., UV$_{max}$(H$_2$O) (nm): 198; JR$^{KBr}$(cm$^{-1}$): 3300, 2950, 2875, 1640, 1555.

EXAMPLE 5

Preparation of the N-benzoyl-PGM

Into a solution of PGM (1,346 mg, 1.33 mmole) in DMF (23.3 mL) there were added succinimido-benzoate (400 mg, 1.825 mmole) and triethylamine (TEA) (0.35 mL) and it was stirred for 24 hours at 25° C. There was added dropwise EtOAc (160 mL) and the resulting suspension was kept stirring for 5 hours. The precipitate was separated by filtration, washed with EtOAc (2×10 mL) and dried. Yield 1.45 g. The product was purified by means of column chromatography on silica gel and elution with the solvent system A. The product-comprising fractions were combined and concentrated by the evaporation of the solvent at reduced pressure. Yield 1.04 g (69.1%).

M.p. 173°–175° C., UV$_{max}$(H$_2$O) (nm): 203, 224 (sh); IR$^{KBr}$(cm$^{-1}$): 3260, 1680, 1515.

EXAMPLES 6–9

In an analogous manner as described in Examples 2–5, there were obtained the following PGM derivatives: capriloyl, caprinoyl, lauroyl and palmitoyl. The principal physical characteristics of said derivatives are represented in Table 2.

TABLE 2

| | | | |
|---|---|---|---|
| Principal physical characteristics of N-capriloyl, N-caprinoyl, N-lauroyl and N-palmitoyl derivatives of PGM. | | | |
| N-acyl-PGM | M.p. °C. | UV$_{max}$ (H$_2$O) (nm) | IR$^{KBr}$ (cm$^{-1}$) |
| capriloyl | 194–195 | 203 | 3280, 2930, 1655, 1638, 1545 |
| caprinoyl | 196–197 | 203 | 2990, 1610, 1580, 1090 |
| lauroyl | 203–205 | 204 | 3280, 2920, 2850, 1655, 1543 |
| palmitoyl | 205–208 | 203 | 3280, 2920, 2845, 1635, 1520 |

EXAMPLE 10

Preparation of the N-stearoyl-PGM

Into a solution of stearic acid (284.5 mg, 1 mmole) in a solvent mixture ethylacetatetetrahydrofuran (1:1, v./v., 25 mL) there were added N-hydroxy-benzotriazole (IIOBt) (162.2 mg, 1.2 mmole) and DCC (247 mg, 1.2 mmole) and it was stirred for 16 hours at 20°–25° C. The obtained precipitate was separated by filtration and it was washed on a filter with EtOAc (2×3 ml). The mother liquor and the extracts were combined and evaporated to dryness at reduced pressure. The crude product (470 mg) was purified by means of column chromatography on silica gel (5 g) and elution with the solvent system chloroform-methanol (100:1, v./v.). There were obtained 350 mg of the purified N-benztriazole-stearate, which was dissolved in DMF (20 mL) and there were added PGM (511 mg, 0.499 mmole) and triethylamine (TEA) (0.13 mL) and the mixture was stirred for 16 hours at 20°–25° C. There resulted a gelatinous precipitate to which there was added EtOAc (88 mL) and the stirring was continued for a further hour. The precipitate was separated by filtration, resuspended in EtOAc (45 mL), stirred for 1 hour and once more filtered off and dried. Yield 621 mg. The product was purified by means of column chromatography on silica gel (8 g) and elution with the solvent system A. The product-containing fractions were combined, the solvent was evaporated at reduced pressure and the product was dried.

Yield 542.5 mg (85%). The product was identical with the product of Example 2.

EXAMPLE 11

Preparation of the sodium salt of N-stearoyl-PGM

N-stearoyl-PGM of Example 2 (1.276.5 mg, 1 mmole) was added to water (20 mL), wherein an equimolar amount of sodium hydroxide had been dissolved. The clear solution was stirred for 1 hour and lyophilized. Yield 1.281 mg.

EXAMPLE 12

Preparation of the sodium salt of N-stearoyl-PGM

In accordance with the process of Example 2, the crude product, obtained upon the precipitation by means of the addition of EtOAc, was suspended in water, neutralized by the addition of sodium hydroxide up to a pH of 7, whereupon the clear solution was charged into a column packed with Sephadex G-25 fine, whereupon it was eluted with water. The fractions, comprising an identical product as in Example 11, were combined and lyophilized.

In an analoguous manner as described in Examples 11 and 12, there were obtained further pharmaceutically acceptable salts.

We claim:

1. N-acyl derivatives of the peptidoglycan monomer of the formula I

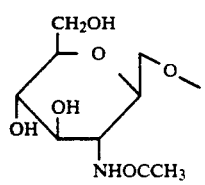

-continued

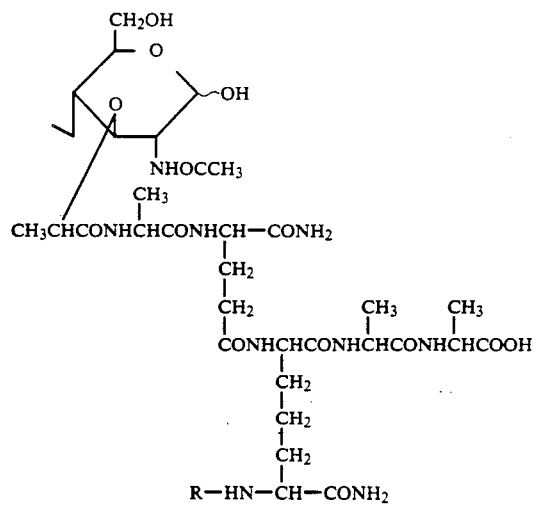

wherein R stands for an acyl group of a straight-chain C2-18 alkyl carboxylic acid, or a branched-chain C5-18 alkyl carboxylic acid, or an unsaturated C12-18 alkenyl carboxylic acid, or a C7-12 aromatic carboxylic, provided that R is other than acetyl and pivaloyl, and pharmaceutically acceptable salts thereof.

2. A compound of formula (I), according to claim 1, wherein R stands for capriloyl.

3. A compound of formula (I), according to claim 1, wherein R stands for caprinoyl.

4. A compound of formula (I), according to claim 1, wherein R stands for lauroyl.

5. A compound of formula (I), according to claim 1, wherein R stands for palmitoyl.

6. A compound of formula (I), according to claim 1, wherein R stands for stearoyl.

7. A compound of formula (I), according to claim 1, wherein R stands for oleoyl.

8. A compound of formula (I), according to claim 1, wherein R stands for benzoyl.

9. A process for the manufacture of N-acyl derivatives of the peptidoglycan monomer of the formula I

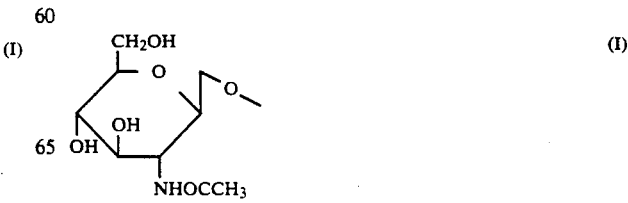

-continued

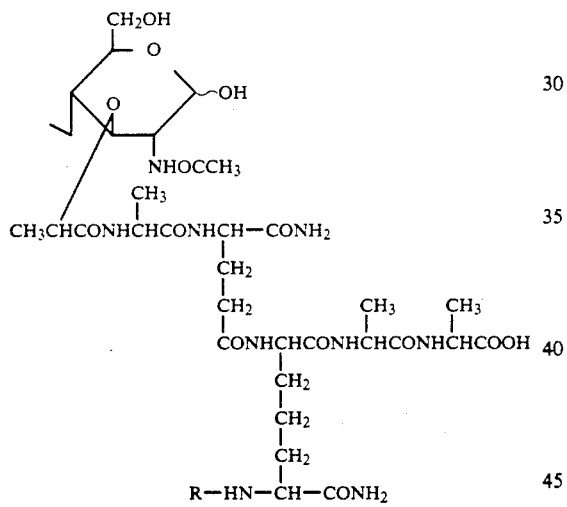

wherein R stands for an acyl group of a straight-chain $C_{2-18}$ alkyl carboxylic acid, or a branched-chain $C_{5-18}$ alkyl carboxylic acid, or an unsaturated $C_{12-18}$ alkenyl carboxylic acid, or a $C_{7-12}$ aromatic carboxylic acid, and pharmaceutically acceptable salts thereof, characterized that PGM of the formula II

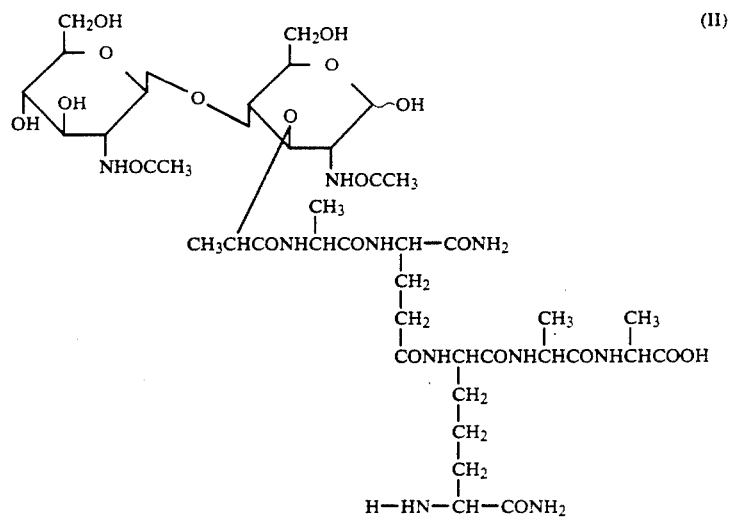

is acylated by means of reacting with an acid

wherein R has the meaning as defined in formula I, and wherein the acid is in activated form, in the presence of a base.

10. A process as claimed in claim 9, wherein the acid (III) is in the form of an anhydride or ester.

11. Immunomdulatory compositions comprising a pharmaceutically active, yet physiologically tolerated dose of a substance of the formula (I) or pharmaceutically acceptable salt thereof as claimed in claim 1.

12. Immunoadjuvant compositions comprising a pharmaceutically active, yet physiologically tolerated dose of a substance of the formula (I) or pharmaceutically acceptable salt thereof as claimed in claim 1.

13. A method of modulation of the immuno-response in humans and warm-blooded animals, which comprises administering an effective amount of a substance of the formula (I) or pharmaceutically acceptable salt thereof as claimed in claim 1, or a composition containing same as an active ingredient in combination with a pharmaceutically acceptable carrier.

14. A method as claimed in claim 18, characterized in that it is performed per i.p. route.

* * * * *